(12) United States Patent
Sommer et al.

(10) Patent No.: US 9,409,357 B1
(45) Date of Patent: Aug. 9, 2016

(54) DEVICES, SYSTEMS, AND METHODS FOR MICROSCALE ISOELECTRIC FRACTIONATION

(71) Applicant: Sandia Corporation, Albuquerque, NM (US)

(72) Inventors: Gregory J. Sommer, Livermore, CA (US); Anson V. Hatch, Tracy, CA (US); Ying-Chih Wang, Pleasanton, CA (US); Anup K. Singh, Danville, CA (US)

(73) Assignee: Sandia Corporation, Albuquerque, NM (US)

( * ) Notice: Subject to any disclaimer, the term of this patent is extended or adjusted under 35 U.S.C. 154(b) by 409 days.

(21) Appl. No.: 13/747,587

(22) Filed: Jan. 23, 2013

Related U.S. Application Data

(62) Division of application No. 12/243,817, filed on Oct. 1, 2008, now Pat. No. 9,005,417.

(51) Int. Cl.
*B29D 7/01* (2006.01)

(52) U.S. Cl.
CPC ....................................... *B29D 7/01* (2013.01)

(58) Field of Classification Search
CPC .... B05D 3/002; B05D 3/061; B05D 2202/00; B29D 7/01
USPC .......................................................... 427/510
See application file for complete search history.

(56) References Cited

U.S. PATENT DOCUMENTS

2004/0112751 A1\* 6/2004 Han et al. ...................... 204/605

OTHER PUBLICATIONS

Sommer et al. "On-Chip Isoelectric Focusing Using Photopolymerized Immobilized pH Gradients" Anal. Chem. May 2008, 80, 3327-3333.\*
Hatch et al. "Integrated Preconcentration SDS-PAGE of Proteins in Microchips Using Photopatterned Cross-Linked Polyacrylamide Gels" Anal. Chem. 2006, 78, 4976-4984.\*

\* cited by examiner

*Primary Examiner* — Robert S Walters, Jr.
(74) *Attorney, Agent, or Firm* — Medley, Behrens & Lewis, LLC

(57) ABSTRACT

Embodiments of the present invention provide devices, systems, and methods for microscale isoelectric fractionation. Analytes in a sample may be isolated according to their isoelectric point within a fractionation microchannel. A microfluidic device according to an embodiment of the invention includes a substrate at least partially defining a fractionation microchannel. The fractionation microchannel has at least one cross-sectional dimension equal to or less than 1 mm. A plurality of membranes of different pHs are disposed in the microchannel. Analytes having an isoelectric point between the pH of the membranes may be collected in a region of the fractionation channel between the first and second membranes through isoelectric fractionation.

11 Claims, 5 Drawing Sheets

DEVICES, SYSTEMS, AND METHODS FOR MICROSCALE ISOELECTRIC FRACTIONATION

CROSS-REFERENCE TO RELATED APPLICATIONS

This application is a divisional application of and discloses subject matter that is related to subject matter disclosed in co-pending parent application U.S. patent application Ser. No. 12/243,817 filed on Oct. 1, 2008 and entitled "DEVICES, SYSTEMS, AND METHODS FOR MICROSCALE ISOELECTRIC FRACTIONATION." The present application claims the priority of its parent application. The parent application is incorporated herein by reference.

STATEMENT REGARDING RESEARCH & DEVELOPMENT

The United States Government has a paid-up license in this invention and the right in limited circumstances to require the patent owner to license others on reasonable terms as provided for by the terms of contract No. DE-AC04-94AL85000 awarded by the U.S. Department of Energy to Sandia Corporation.

TECHNICAL FIELD

Embodiments of the invention relate generally to microfluidic devices, and more specifically to methods and systems for performing microscale isoelectric fractionation.

BACKGROUND

Biological diagnostic techniques frequently require a purification process be performed on a sample prior to analysis. An unprocessed serum sample may contain as many as $10^5$-$10^6$ different protein species at various concentrations. In proteomic diagnostics, accordingly, analytes of interest in a serum sample may be obscured by other protein species in the sample. Accordingly, microfluidic assay techniques typically require an off-chip purification technique such as dialysis, centrifugation, or desalting, prior to analysis. Requiring an off-chip purification step may limit the usefulness of microfluidic analysis techniques. Without the ability to receive and analyze a raw sample, the microfluidic device may not also serve as the collection point for a raw sample. Rather, the raw sample may first be processed in a macroscale device and later introduced into the microfluidic device for analysis.

Isoelectric fractionation is a technique for electrokinetically separating analytes in solution based on their isoelectric point. The isoelectric point of an analyte is the pH at which the analyte acquires no net charge. For example, proteins are composed of a variety of amino acid groups which act together to give the protein its overall charge. At the isoelectric point of the protein, the exchange of protons with the solution (protonation and deprotonation) will be balanced, and the protein acquires no net charge. At a pH below the isoelectric point of the protein, protonation typically dominates and the protein acquires a net positive charge. At a pH above the isoelectric point of the protein, deprotonation dominates and the protein acquires a net negative charge.

FIG. 1 depicts a tube 100 suitable for macroscale isoelectric fractionation. The tube 100 is typically around a half-inch in diameter, and several inches long. The tube 100 includes individual compartments 105, 110, 115, and 120. Each chamber may be connected to the next by, for example, threaded connectors. Each compartment is separated from the next by a membrane cartridge 106, 111, 116, and 121, respectively. Each membrane cartridge 106, 111, 116, and 121 contains a porous membrane having a constant and specific pH value. The membrane cartridges and compartments may have O-rings or other sealing devices separating the individual compartments. The pH values of the membranes increase from a first end 130 of the tube 100 to a second end 135 of the tube 100. A sample in solution is loaded into the tube at any point and is separated using electrophoretic transport.

Electrophoretic transport involves applying an electric field across the tube 100. Accordingly, an electric field 140 is generated by applying a voltage across an anode 145 at the first end 130 of the tube and a cathode 150 at the second end 135 of the tube 100. Positively charged analytes will be transported through the tube 100 in the direction of the electric field 140, toward the cathode 150, and negatively charged analytes in the opposite direction. The analytes will pass through the membrane cartridges 106, 111, 116, 121 until they reach the compartment corresponding to their isoelectric point, at which point they will have no net charge, and will no longer move through the tube 100 by electrophoresis. In this manner, the analytes may be separated according to their isoelectric point. Following fractionation, the isolated samples in the compartments 105, 110, 115, and 120 may be removed for further analysis.

Macroscale isoelectric fractionation, as described above and with reference to FIG. 1, may take several hours to complete a fractionation. Furthermore, a large sample volume may be required to populate the macroscale compartments. The macroscale device may also be difficult to integrate with a microfluidic device. The membranes in the macroscale device are also polymerized in a chemical process with a support disk which is placed in the device following fabrication. The macroscale membrane must be mechanically robust to withstand the physical assembly steps. This limits the materials that may be used to form the macroscale membrane.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known materials, chemical components, buffers or other additives, analytes, electrical components, material processing and fabrication techniques, have not been shown in detail in order to avoid unnecessarily obscuring the described embodiments of the invention.

Embodiments of the present invention provide devices and methods for performing microscale isoelectric fractionation (μIF). Devices according to embodiments of the present invention generally include a channel having a dimension of around 1 mm or less. In some embodiments, 500 μm or less. In some embodiments, the devices have a dimension of around 100 μm or less. Other dimensions may be used, as generally described below.

Figure 1:
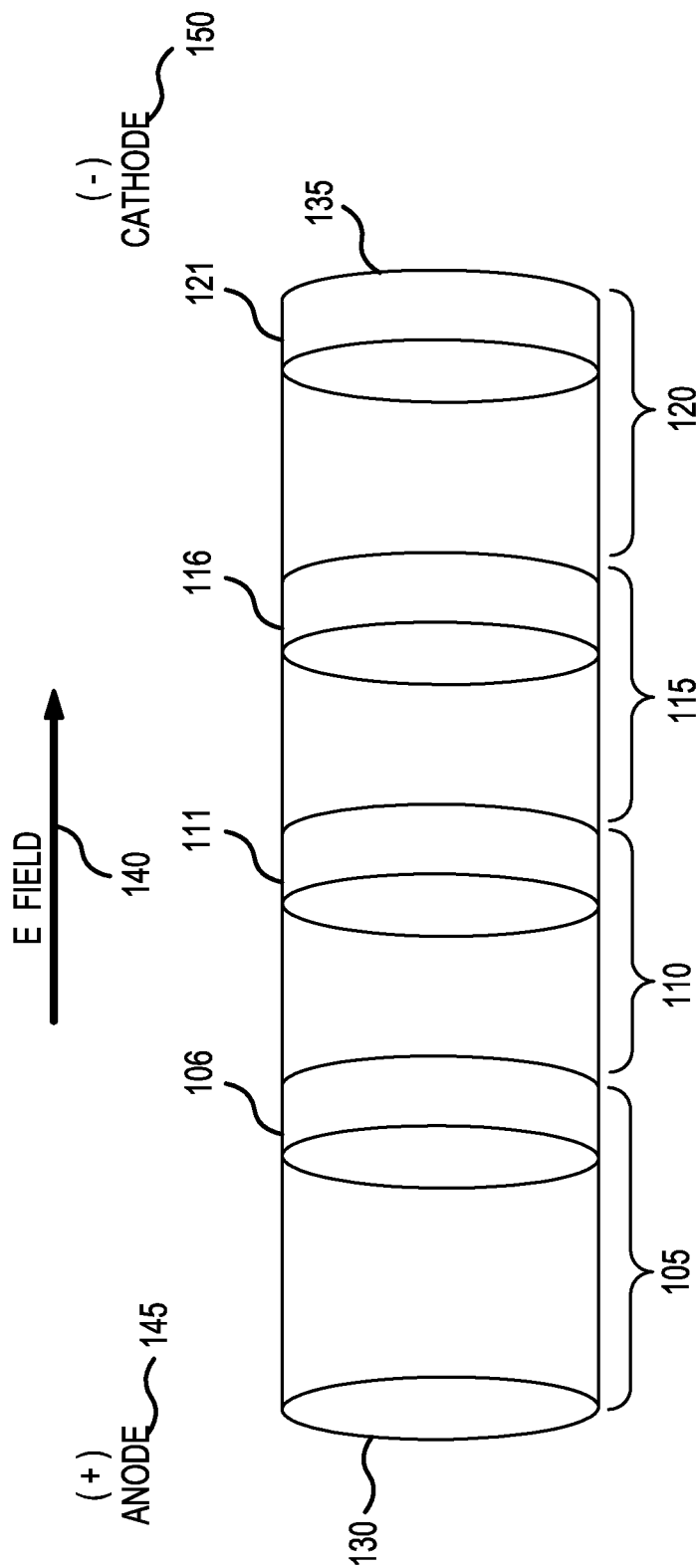
FIG. 1 is a schematic illustration of a macroscale isoelectric fractionation device according to the prior art.
Figure 2:
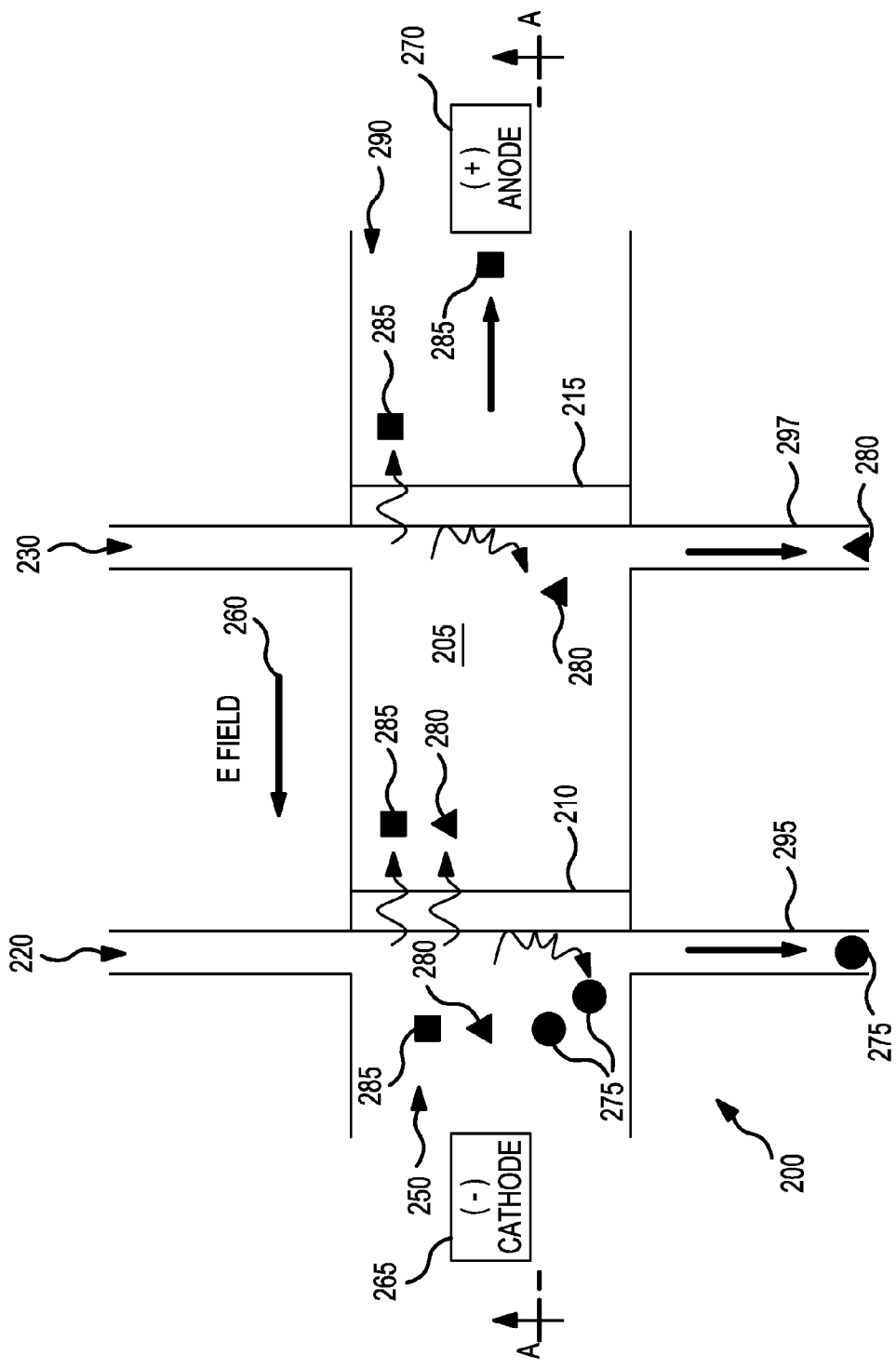
FIG. 2 is a schematic illustration of a microscale isoelectric fractionation device according to an embodiment of the present invention.

FIG. 2 depicts a microchannel structure 200 according to an embodiment of the present invention. A microchannel 205 generally may range in dimensions of depth from 1 μm to 1 mm, 1 μm to 500 μm in some embodiments, and 10 μm to 300 μm in other embodiments. The width of the microchannel 205 generally may range from 1 μm to 1 cm, 1 μm to 1 mm in other embodiments, 1 μm to 500 μm in some embodiments, and 10 μm to 300 μm in other embodiments. The width and depth of the microchannel are generally selected to obtain the desired flow characteristics in the channel and provide sufficient volume for the amount of sample or target analytes to be received by the channel. The length of the microchannel 205 generally may range from 10 μm to 10 cm, from 100 μm to 1 cm in other embodiments. Generally, the length of the microchannel 205 is selected to accommodate a desired number of membranes and volume of channel between membranes that will be suitable for the application and volume of target analyte to be received by the microchannel 205.

Figure 3:
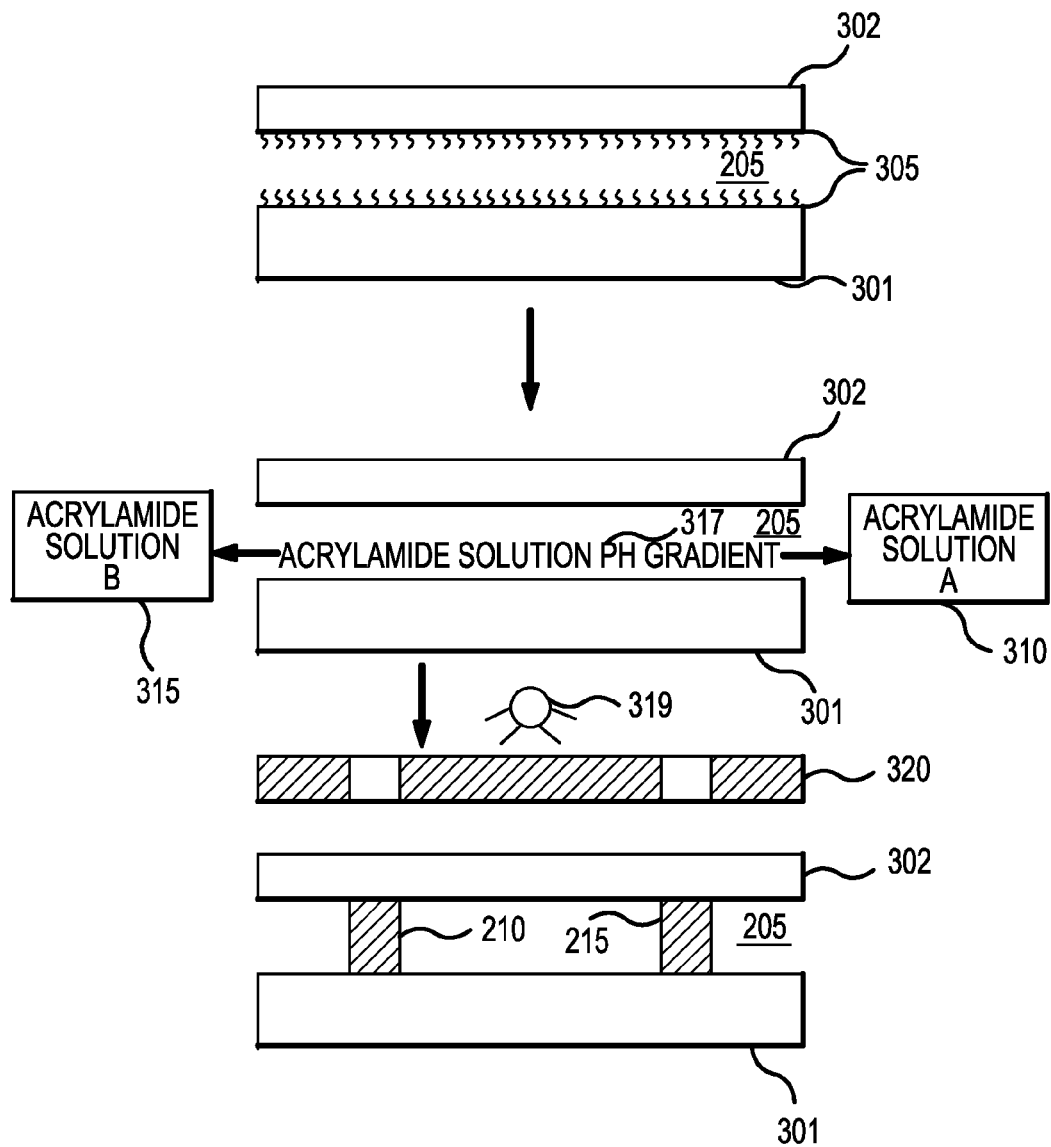
FIG. 3 is a schematic illustration of a method for making a microscale isoelectric fractionation device according to an embodiment of the present invention.
Figure 4:
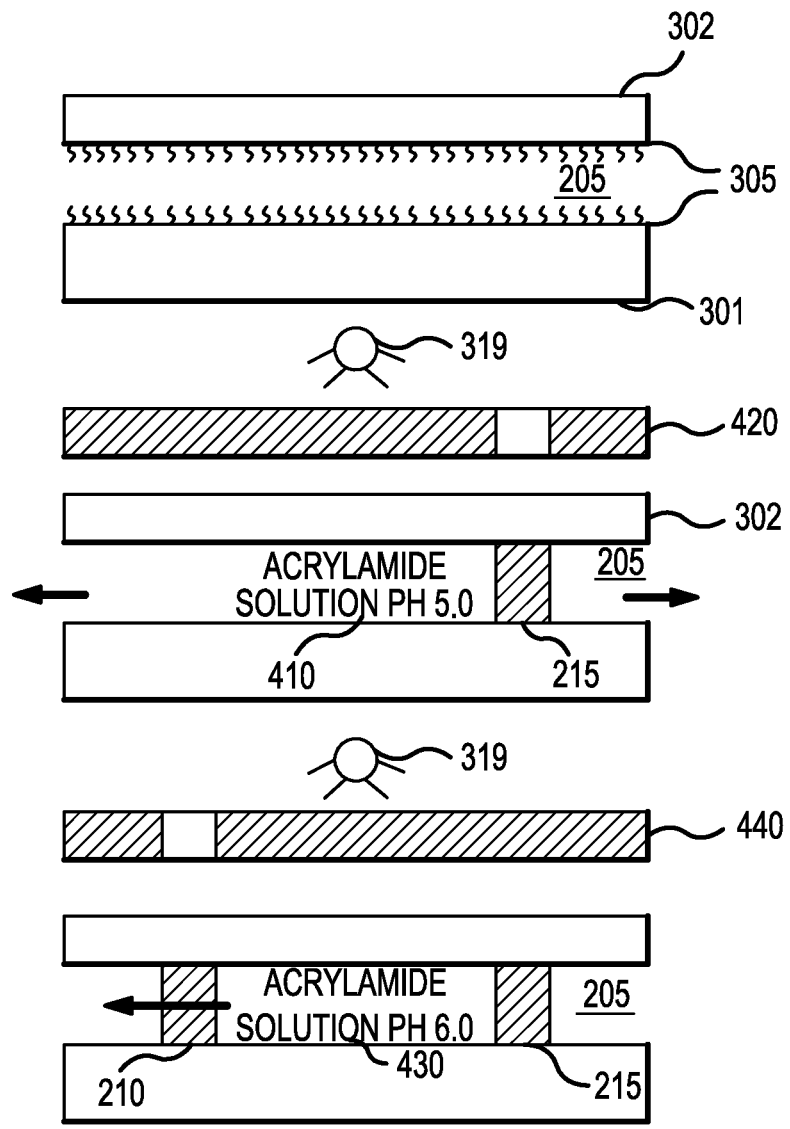
FIG. 4 is a schematic illustration of a method for making a microscale isoelectric fractionation device according to an embodiment of the present invention.

Two membranes 210, 215 are positioned in the microchannel 205. As will be described further below, the membranes each have a different pH, making the microchannel structure 200 suitable for performing isoelectric fractionation. General features of the microchannel structure 200 having been described, a discussion of embodiments for making the microchannel structure 200, including the membranes 210, 215 will now be discussed with reference to FIGS. 3 and 4. FIGS. 3 and 4 generally show a cross-section of the microchannel structure 200 shown in FIG. 2 along the line A-A during and following the formation of the membranes 210, 215.

The channel 205 itself may be formed by generally any material suitable for forming a channel of the dimensions described above and for containing the membranes which will be further described. Glass, including fused silica, may be used to form the channel 205 in some embodiments. In the embodiments shown in FIGS. 3 and 4, and as known in the art, a photolithography mask may be used to generate the pattern of the microchannel 205, as well as other channels depicted in FIG. 2. The glass substrate 301 may then be etched to form the microchannel 205 using methods known in the art including dry or wet etching. In other embodiments, a maskless process may be used.

Accordingly, a bottom surface and sidewalls of the microchannel 205 may be defined by the glass substrate 301. A top surface of the microchannel 205 may be defined by a material integral to the substrate 301 or adhered or bonded to the substrate 301, such as an upper substrate 302. The upper substrate 302 may also be glass, fused silica, PDMS, PMMA, cyclic olefin copolymer, polycarbonate, or other material compatible with the techniques and processes described herein. At least one surface of the channel 205 may be formed of a transparent material for ease in exposing all or portions of the channel 205 to a light source, as will be further described below.

After forming the microchannel 205, the surfaces of the microchannel 205 may be treated to promote adhesion to the membranes 210, 215. In some embodiments, the membranes 210, 215 are polyacrylamide membranes and a surface treatment prior to the formation of the membranes may include coating one or more of the interior surfaces of the microchannel 205 with an acrylate-terminated self-assembled monolayer using a process of incubation, rinsing, and drying. In one embodiment, the surface treatment includes conditioning the microchannel 205 with 1M aqueous NaOH, rinsing with deionized water, and vacuum drying the microchannel 205. Introduction of fluids into the microchannel 205 may occur through any known methods, including by pressure-driven flow. A 2:3:5 (volume ratio) mixture of 3-(trimethoxysilyl) propyl methacrylate, glacial acetic acid, and deionized water that has been sonicated and degassed, is then loaded into the microchannel 205. The microchannel 205 is incubated for about 30 minutes, rinsed with a 3:7 (v/v) mixture of acetic acid and water, rinsed with deionized water, and dried with a vacuum. This process leaves an acrylate terminated self-assembled monolayer 305 on the surfaces of the microchannel 205. The self-assembled monolayer 305 is shown in FIG. 3 for illustrative purposes only, and is not to scale. Other solutions, incubation times, and rinsing and drying procedures may be used to deposit the self-assembled monolayer 305. In some embodiments, the self-assembled monolayer 305 may not be necessary for adequate adhesion of the microchannel 205 surfaces with the membranes.

The membranes 210, 215, according to embodiments of the present invention are regions of polyacrylamide gels. Generally, the gels are formed by introducing an aqueous solution including acrylamide monomer, bisacrylamide crosslinker, and a photoinitiator into the microchannel 205. The membranes 210, 215 may then be formed by polymerizing the solution by exposing the desired membrane area to a UV light source. The pH of the gel may be controlled by introducing calculated amounts of acrylamido buffers (such as IMMOBILINE®) into the aqueous acrylamide monomer solution. Various embodiments of suitable aqueous solutions and methods for polymerizing acrylamide gel regions are described in co-pending application Ser. No. 12/182,755 filed Jun. 30, 2008, entitled "Methods for providing and using solution gradients in microchannels," and naming inventors Anson V. Hatch, Gregory J. Sommer, Amy E. Herr, and Anup K. Singh, the entire contents of which are hereby incorporated by reference for any purpose. The table below describes embodiments of suitable solutions at various pH levels. The quantity of acrylamide and the cross-linker bisacrylamide are listed as a total concentration percentage (T) and a concentration of the crosslinker (C), which can be calculated using the following equations:

$$\% \text{ Total}(T) = \frac{g \text{ (acryl} + bis)}{100 \text{ mL}}, \% \text{ Crosslinker}(C) = \frac{g \text{ } bis}{100 \text{ g (acryl} + bis)}$$

The pH levels recited are by way of example only, and generally any pH level may be achieved by adjusting the recipe accordingly.

TABLE 1

Recipes for solutions for generating membranes having pH 3.8 and 7.0, respectively

| Reagent | pH 3.8 solution | pH 5.0 solution | pH 6.0 solution | pH 7.0 solution |
|---|---|---|---|---|
| Acrylamide/ bisacrylamide | 5% T, 2.6% C | 5% T, 2.6% C | 5% T, 2.6% C | 5% T, 2.6% C |
| IMMOBILINE® buffer - pK 3.6 | 12.7 mM | 8.98 mM | 6.68 mM | 4.4 mM |
| IMMOBILINE® buffer - pK 4.6 | — | 3.86 mM | 7.08 mM | 10.3 mM |

TABLE 1-continued

Recipes for solutions for generating membranes
having pH 3.8 and 7.0, respectively

| Reagent | pH 3.8 solution | pH 5.0 solution | pH 6.0 solution | pH 7.0 solution |
|---|---|---|---|---|
| IMMOBILINE® buffer - pK 6.2 | 7.48 mM | 5.56 mM | 3.96 mM | 2.36 mM |
| IMMOBILINE® buffer - pK 7.0 | — | 1.56 mM | 2.87 mM | 4.17 mM |
| IMMOBILINE® buffer - pK 9.3 | — | 4.85 mM | 8.43 mM | 12.1 mM |
| VA-086 photoinitiator | 0.2% (w/v) | 0.2% (w/v) | 0.2% (w/v) | 0.2% (w/v) |

In one embodiment, the membranes 210, 215 are formed by flowing acrylamide monomer solutions of different pH through side channels (not shown) flanking the microchannel 205. This is illustrated schematically in FIG. 3 by the acrylamide solution A 310 and acrylamide solution B 315. The self-assembled monolayer on the surfaces of the microchannel 305 is omitted for clarity. Acrylamide solution A 310 and acrylamide solution B 315 have different pH values. For example, acrylamide solution A 310 may have a pH of 3.8 while the acrylamide solution B 315 has a pH of 7. Through diffusion, a gradient 317 of acrylamide solution having varying pH develops along the microchannel 205.

The microchannel 205 containing the acrylamide solution pH gradient 317 may then be exposed to a UV light source 319 through a mask 320. The regions of the solution exposed to the UV light source 319 are polymerized and form the membranes 210 and 215. By selecting the pH of acrylamide solutions A 310 and B 315, and the position along the microchannel 205 for UV light exposure, the pH of the membranes 210 and 215 can be selected. The pH of membrane 210 may be 6.0 while the pH of the membrane 215 may be 5.0 in the example of FIG. 3. In other embodiments, a shaped and focused beam, such as a laser, is used to polymerize the solution and form the membranes 210 and 215, and the mask 320 may not be necessary. The membranes 210 and 215 accordingly fill the cross-sectional area of the microchannel 205, adhering to each of the interior surfaces of the microchannel 205. The membranes have a width defined by their exposure to the polymerizing light source and may generally be 20-50 μm wide, although wider membranes may also be fabricated. Narrower membranes may also be fabricated if appropriate light exposure techniques are used or found that allow for a narrower region of polymerization.

Following polymerization, unpolymerized solution may be flushed out of the microchannel 205. Solution may be removed from the inlet and outlet of the microchannel 205, through side channels, such as the channels 220 and 230 in FIG. 2.

Embodiments of methods for forming discrete membranes of different pH using an acrylamide solution pH gradient 317 and resultant devices are described in co-pending application Ser. No. 12/182,755 filed Jun. 30, 2008, entitled "Methods for providing and using solution gradients in microchannels," and naming inventors Anson V. Hatch, Gregory J. Sommer, Amy E. Herr, and Anup K. Singh, the entire contents of which are hereby incorporated by reference for any purpose.

Accordingly, a process described above with reference to FIG. 3 simultaneously forms the membranes 210 and 215 having different pH levels by establishing a pH gradient across the channel 205, then polymerizing a plurality of areas during a single exposure. Of course, multiple exposures of the gradient could also be made to form the membranes 210 and 215 in other embodiments. In still other embodiments, described below with reference to FIG. 4, the membranes 210 and 215 are formed in separate exposures without the need to establish a gradient of solution across the microchannel 205.

The microchannel 205 and self-assembled monolayer 305 are formed as described above with reference to FIG. 3. A first acrylamide solution 410 is then introduced into the microchannel 205 for formation of the membrane 215. The first solution is of the desired pH for the membrane 215, pH 5.0. The microchannel 205 containing the acrylamide solution of pH 5.0 may then be exposed to a UV light source 319 through a mask 420, polymerizing the membrane 215. As described above with reference to FIG. 3, in other embodiments, a laser is used to polymerize the solution and form the membranes 215, and the mask 420 may not be necessary.

The first acrylamide solution 410 having a pH of 5.0 is then flushed out of the microchannel 205 through the inlet, outlet, or side channel such as the side channels 220 and 230 in FIG. 2. A second acrylamide solution 430 having the desired pH for the membrane 210, a pH of 6.0 in the embodiments shown in FIG. 4, is then introduced into the microchannel 205. The microchannel 205 is again exposed to the UV light source 319 through a mask 440 to polymerize the membrane 210.

As in the process described above with regard to FIG. 3, the process shown in FIG. 4 results in membranes 210 and 215 that fill the cross-sectional area of the microchannel 205, adhering to each of the interior surfaces of the microchannel 205. The membranes have a width defined by their exposure to the polymerizing light source and may generally be 20-50 μm wide, although wider membranes may also be fabricated. Narrower membranes may also be fabricated if appropriate light exposure techniques are used or found that allow for a narrower region of polymerization.

Although the methods described above result in the formation of two membranes 210 and 215, embodiments of the present invention may be employed to form any number of membranes in a microchannel, including 1, 2, 3, 4, 5, 6, 7, 8, 9, and 10 membranes. Some embodiments may have up to 20 membranes in a microchannel. Still more membranes may be formed in the channel in accordance with the length of the channel and the desired application, up to 100 membranes or even more. A well-controlled gradient may be generated up to centimeters long and membranes may be fabricated as close as about 100 microns apart. The membranes 210 and 215 described above have pH values—5.0 and 6.0—that are 1 pH unit apart. However, embodiments of the present invention may be used to form membranes in a microchannel having pH values that are closer together or further apart, with the closest spacing being about 0.01 pH unit. To achieve the smaller resolutions, membranes may be formed by generating a shallow gradient by diffusion and then photopolymerizing membranes at different points along the gradient . . . . Accordingly, the membrane 210 may have a pH of 5.0, for example, while the membrane 215 has a pH of 5.1. Accordingly, membranes may be provided having substantially any pH resolution from about 0.1 pH unit on up. As will be described further below, the selection of pH of the membranes will affect the resolution of the isoelectric fractionation that may be performed in the microchannel 205.

After formation of the membranes 210, 215 through using embodiments of the methods described above, the microchannel 205 may be filled with an aqueous solution of acrylamide monomer at neutral pH and the entire microchannel 205 exposed to the UV light source 319 to photopolymerize an acrylamide gel throughout the microchannel 205. The microchannel 205 would then contain a continuous gel with regions of specific pH at the membranes 210, 215. In other embodiments, the microchannel 205 is not filled with acrylamide gel, and an aqueous or other fluid medium may fill the channel, including the region between the membranes 210 and 215.

The membranes 210, 215 generally block fluid flow in the microchannel 205; however, the membranes 210, 215, formed of polymerized acrylamide solution, are sufficiently porous to allow analytes to pass through the membrane. The microchannel structure 200 shown in FIG. 2 may accordingly be used to perform microscale isoelectric fractionation. Having described embodiments for making the microchannel structure 200 above, methods for performing isoelectric fractionation will now be described with reference to FIG. 2.

A sample is introduced to the microchannel 205, at the first end 250, or any location along the microchannel 205, or any combination of microchannel locations. The sample may generally be any fluid containing target analytes for separation by the isoelectric fractionation techniques described below. Samples accordingly may include serum, urine, saliva, or other biological fluid samples. Analytes that may be separated according to the techniques described below include proteins, peptides, or other species in the sample that may be separated according to their isoelectric point.

The sample may be introduced into the microchannel 205 through any mechanism, including pressure driven flow. The sample may be stored in a sample reservoir in fluid communication with the microchannel 205. The sample reservoir may be integral with or separable from the microchannel structure 200. Analytes are then drawn into the microchannel 205, toward the membranes 210 and 215 using electrophoresis. An electric field 260 is generated in the microchannel 205 by applying a voltage between two electrodes 265, 270. Any suitable voltage generator and electrodes may be used to generate the electric field 260, and the electrodes 265, 270 may be integral to the microchannel structure 200, or they may be separate from the structure 200 and placed in sufficient proximity to the structure 200 to generate the electric field 260 in the microchannel 205. The particular voltage used will depend on the spacing of the electrodes 265, 270 and the analytes to be transported. In one embodiment, an electric field 260 of 330 V/cm may be sufficient to transport analytes through the microchannel 205.

Three analytes 275, 280, and 285 having different pH values are shown in FIG. 2. The analyte 275 has an isoelectric point greater than 6.0. The analyte 280 has an isoelectric point between 5.0 and 6.0. The analyte 285 has an isoelectric point less than 5.0. Although the analytes 275, 280, and 285 are schematically illustrated in FIG. 2 as a circle, triangle, and square, respectively, the shapes are for ease of illustration only and do not reflect actual analyte shapes, and analytes having different isoelectric points will not necessarily have different shapes.

Under the influence of the electric field 260, the analytes 285, 280, and 275 are drawn from the first end 250 of the microchannel 205 toward the second end 290 of the microchannel. In higher pH environments, proteins are more negatively charged; accordingly, the proteins will be drawn toward the more positive electrode until they reach their isoelectric point at which they carry substantially no net charge. For example, the analyte 275 will not traverse through the membrane 210. Recall the membrane 210 has a pH of 6.0 and the analyte 275 has an isoelectric point of greater than 6.0. Accordingly, the analyte 275 will remain in the area of the microchannel 205 between the first end 250 and the membrane 210. The analytes 280 and 285, however, have isoelectric points less than 6.0, and will be drawn through the membrane 210 as shown, and toward the second membrane 215.

The analyte 280, having an isoelectric point greater than 5.0, will not traverse through the second membrane 215 which has a pH of 5.0. Accordingly, the analyte 280 will remain in the region of the microchannel 205 between the first membrane 210 and the second membrane 215. The analyte 285, having an isoelectric point less than 5.0 will be drawn through the membrane 215, and will proceed toward the second end of the microchannel 290. The analyte 285 may be transported out of the microchannel 205 and into a waste or other reservoir in fluid communication with an outlet of the microchannel 205.

During the fractionation process, one or more E-fields generally perpendicular to the fractionation channel may also be applied to help retain analytes within the fractionation channel. This would reduce loss occurring at any cross-channel intersections by, for example, diffusion outside of the centrally applied field.

The micoscale isoelectric fractionation techniques described may also enable preconcentration of analytes. The local concentration of an analyte within each pH range may be increased with continued fractionation. The concentrated analyte may then be used in any analytic or other technique.

In this manner, analytes having an isoelectric point over 6.0 will be collected in the region between an inlet of the microchannel 205 and the membrane 210. Analytes having an isoelectric point between 6.0 and 5.0 will be collected in the region between the membranes 205 and 210. Analytes having an isoelectric point less than 5.0 will be collected in a region following the membrane 215, or in a waste reservoir. Although three regions of separation are achieved in the embodiment of FIG. 2, any number of different regions may be established of any pH resolution by selecting an appropriate number and pH value of membranes in the microchannel.

Once fractionated, analytes in the various regions may be transported to other locations. For example, the analyte 275 may be transported through an analyte collection microchannel 295. Transport through the analyte collection microchannel 295 may be achieved by, for example, applying an electric field (not shown) along the analyte collection microchannel sufficient to transport the analyte 275 by electrophoresis. In a similar manner, the analyte 280 may be transported through the analyte collection microchannel 297 by applying an electric field along the analyte collection microchannel sufficient to transport the analyte 280 along the analyte collection microchannel. The analyte collection microchannels may be placed at any location in fluid communication with the fractionation microchannel 205 containing the separated analytes. As shown in FIG. 2, the analyte collection microchannels 295, 297 may be placed in proximity to the membranes 210, 215. However, the analyte collection microchannel 295 may generally be coupled to the microchannel 205 at any location between an inlet of the microchannel and the membrane 210, while the analyte collection microchannel 297 may be coupled to the microchannel 205 at any location between the membranes 210, 215.

As described above, microscale isoelectric fractionation may separate analytes on-chip through selected electrophoretic migration of the analytes through pH-specific polyacrylamide membranes. The membranes restrict molecules having isoelectric points below the pH of the membrane. By designing microfluidic channels having a serial array of membranes at various pH values, analytes may be separated and isolated into corresponding pH ranges. While macroscale isoelectric fractionation may take several hours to fractionate, microscale isoelectric fractionation may take only minutes due to the reduced length scales used.

Embodiments of devices and methods conducting microscale isoelectric fractionation in a fractionation channel have been described above. Analytes may be separated according to their isoelectric point, allowing for pre-treatment of a sample containing a wide variety of analytes, such as serum or urine. Once fractionated, analytes of a particular pH range may be transported from the fractionation channel 205 for use in other analytic techniques. Since the fractionation occurred in a microfluidic device, the analytes of interest may be transported to analysis modules on the same chip, which may save time and cost.

Figure 5:
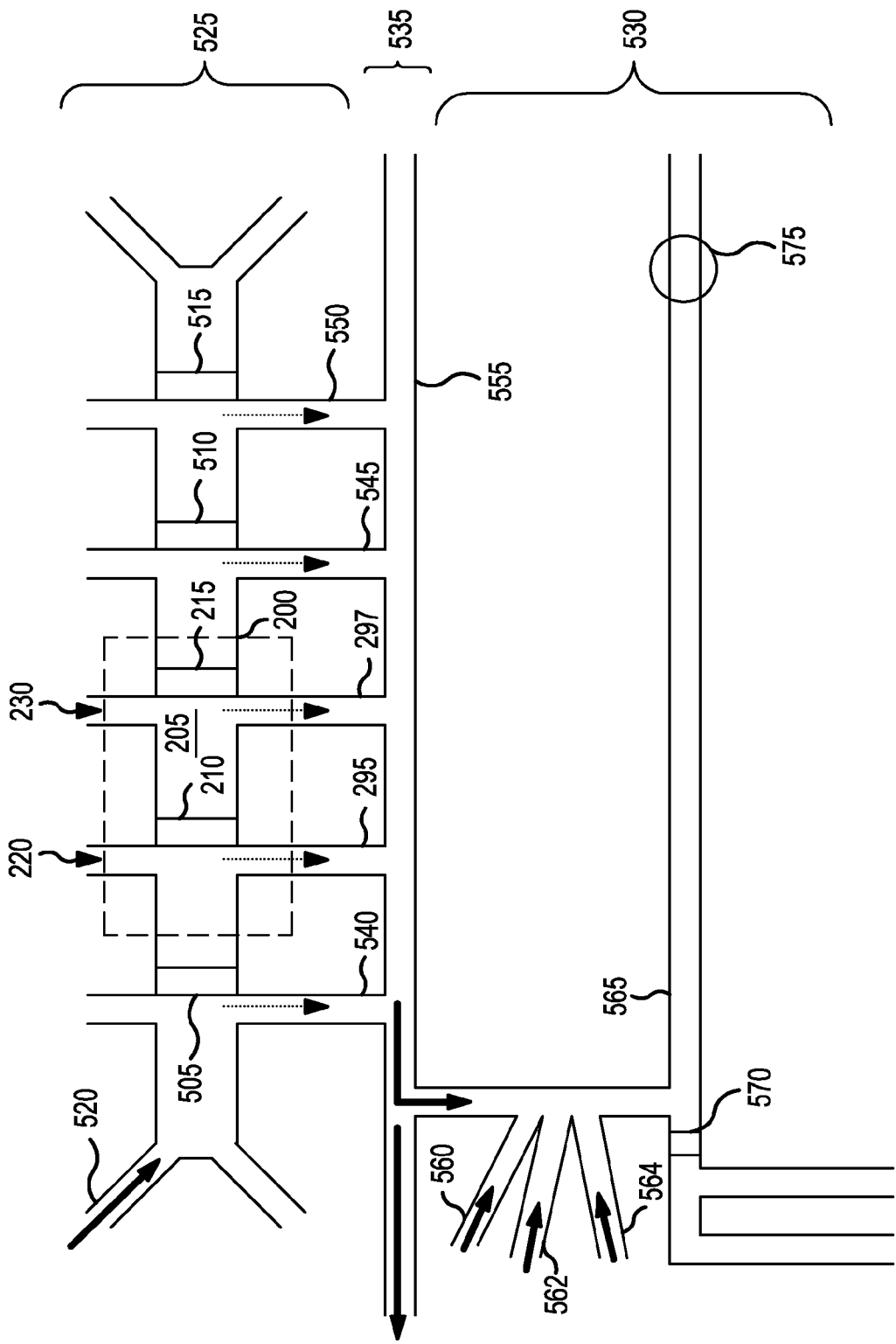
FIG. 5 is a schematic illustration of a microfluidic system according to an embodiment of the present invention.

FIG. 5 depicts an example microfluidic system for analyte analysis. A preparation module 525 is used to prepare analytes for analysis by an assay module 530. A transport module 535 is in fluidic communication with both the preparation module 525 and the assay module 530 and is used to transport analytes from the preparation module 525 to the assay module 530. The preparation module 525, transport module 535, and assay module 530 may all be formed on a same microfluidic device substrate. Alternatively, the modules may be on separate substrates and fluidically connected.

The preparation module 525 is used to separate one or more analytes of interest from other species in a sample. Accordingly, microscale isoelectric fractionation is performed in the preparation module 525 according to methods described above. The microchannel structure 200 of FIG. 2 is shown as part of the preparation module 525, with the microchannel 205 used for fractionation including further membranes 505, 510, and 515 along with the membranes 210 and 215. A sample inlet 520 is shown for introducing the sample to the fractionation microchannel 205. As described above, analytes will be separated in the microchannel 205 according to their isoelectric point into zones separated by the membranes 505, 210, 215, 510, and 515.

Analytes having a certain isoelectric point range may then be moved into the transport module through analyte collection microchannels 540, 295, 297, 545, and 550. Transport may occur through any means, including pressure or pump driven flow, or electrophoresis. The transport module 535 includes transport channel 555. So, for example, analytes having an isoelectric point of between 5.0 and 6.0 may be fractionated into the region between the membranes 210 and 215 as described above. Those analytes may then be transported into the transport channel 555 for analysis. Although only one assay module 530 is shown in FIG. 5, the transport module 535, including the transport channel 555, may connect to any number of assay modules 530. The collected analytes from the fractionation channel 525 may be transported to a selected assay module.

Turning now to the assay module 530, analytes from the transport channel 555 are introduced into the assay module 530 and may be mixed with reagents introduced at reagent introduction channels 560, 562, 564. The specific reagents used will depend on the analyte and the assay technique performed by the assay module 530. In the embodiment shown in FIG. 5, the assay module 530 performs an electrophoretic assay. The analytes are transported into a separation channel 565 and may be preconcentrated at a preconcentration membrane 570. As known in the art, the analytes in the separation channel 565 may then be separated using polyacrylamide gel electrophoresis (PAGE). A target analyte may be detected using fluorescence detection at a detection region 575.

Other microfluidic components may be integrated into the microfluidic system of FIG. 5 including pumps, valves, reservoirs, inlets, outlets, mixing chambers, and channels. The ability to conduct microscale isoelectric fractionation may facilitate integration of the technique with other microfluidic transport and analysis techniques.

As described above, sample may be introduced at an inlet 520, fractionated in the preparation module 525 to group analytes in the sample according to isoelectric point. Only analytes having a certain range of isoelectric points may then be transported in the transport module 535 to the assay module 530 for analysis. In this manner, a sample may be prepared on a microfluidic chip for later analysis on the same chip or within the same microfluidic system. Off-chip sample preparation processes may be reduced or eliminated.

From the foregoing it will be appreciated that, although specific embodiments of the invention have been described herein for purposes of illustration, various modifications may be made without deviating from the spirit and scope of the invention.

What is claimed is:

1. A method for forming a series of pH-specific membranes in a microchannel, the method comprising:
   introducing a first aqueous acrylamide monomer solution into the microchannel having a first pH;
   polymerizing the first aqueous acrylamide monomer solution at a first location in the microchannel to generate a first membrane having the first pH;
   removing a non-polymerized portion of the first aqueous acrylamide monomer solution from the microchannel;
   introducing a second aqueous acrylamide monomer solution into the microchannel having a second pH;
   polymerizing the second aqueous acrylamide monomer solution at a second location in the microchannel to generate a second membrane having the second pH;
   removing a non-polymerized portion of the second aqueous acrylamide monomer solution from the microchannel; and
   filling the microchannel with a third aqueous acrylamide monomer solution having a third pH, wherein the third aqueous acrylamide monomer solution is located in the microchannel between the first membrane and the second membrane, and the first pH, the second pH, and the third pH are different.

2. The method according to claim 1 further comprising, prior to introducing the first aqueous acrylamide monomer solution into the microchannel:
   coating at least one interior surface of the microchannel with an acrylate-terminated self-assembled monolayer.

3. The method according to claim 1 wherein the first aqueous acrylamide monomer solution comprises acrylamide, bisacrylamide, a photoinitiator, and a first concentration of acrylamido buffer, wherein the first concentration of acrylamido buffer controls the first pH of the first membrane and the second aqueous acrylamide monomer solution comprises acrylamide, bisacrylamide, a photoinitiator, and a second concentration of acrylamido buffer, wherein the second concentration of acrylamido buffer controls the second pH of the second membrane.

4. The method according to claim 1 wherein the act of polymerizing the first aqueous acrylamide monomer solution at the first location comprises exposing the first location to a UV light source.

5. The method according to claim 4 wherein the act of exposing the first location to a UV light source includes using a mask to illuminate the first location.

6. The method according to claim 4 wherein the act of exposing the first location to a UV light source includes illuminating the first location with a beam of light.

7. The method according to claim 1 wherein the first membrane and second membrane each have a width less than or equal to 50 μm.

8. The method according to claim 1, wherein the act of polymerizing the second aqueous acrylamide monomer solution at the second location comprises exposing the second location to a UV light source.

9. The method according to claim 8, wherein the act of exposing the second location to the UV light source includes using a mask to illuminate the second location.

10. The method of claim 1, wherein the microchannel has a width of between 1 μm and 500 μm.

11. The method of claim 1, wherein the third pH is a neutral pH.

* * * * *